(12) United States Patent
Eguchi et al.

(10) Patent No.: US 8,078,432 B2
(45) Date of Patent: Dec. 13, 2011

(54) BINDING EVALUATION METHOD FOR MACROMOLECULAR COMPOUND

(75) Inventors: Haruki Eguchi, Tokyo (JP); Toshikazu Yano, Sendai (JP)

(73) Assignee: Ishikawajima-Harima Heavy Industries Co., Ltd (JP)

( * ) Notice: Subject to any disclaimer, the term of this patent is extended or adjusted under 35 U.S.C. 154(b) by 975 days.

(21) Appl. No.: 11/571,968

(22) PCT Filed: Jul. 1, 2005

(86) PCT No.: PCT/JP2005/012200
§ 371 (c)(1),
(2), (4) Date: Jan. 11, 2007

(87) PCT Pub. No.: WO2006/006427
PCT Pub. Date: Jan. 19, 2006

(65) Prior Publication Data
US 2008/0032419 A1   Feb. 7, 2008

(30) Foreign Application Priority Data

Jul. 13, 2004   (JP) ................................ 2004-205746

(51) Int. Cl.
G06F 7/60   (2006.01)
G06G 7/60   (2006.01)
(52) U.S. Cl. ................................ 703/2; 703/11; 702/27
(58) Field of Classification Search ........................ None
See application file for complete search history.

(56) References Cited

U.S. PATENT DOCUMENTS

2002/0062155 A1   5/2002   Itai et al. ............................ 700/1

FOREIGN PATENT DOCUMENTS

EP   1 010 681 A1   6/2000
WO   WO 97/24301 A1   7/1997

OTHER PUBLICATIONS

Huang et al. Anti-HIV Agents That Selectively target Retroviral Nucleocapsid Protein Zinc Fingers without Affecting Cellular Zinc Finger Proteins. Journal of Medicinal Chemistry vol. 41, pp. 1371-1381 (1998).*
Vinter Extended electron distributions applied to the molecular mechanics of some intermolecular interactions. Journal of Computer Aided Molecular Design vol. 8, pp. 653-668 (1994).*
MacKerell et al. All-Atom Empirical Potential for Molecular Modeling and Dynamics Studies of Proteins Journal of Physical Chemistry B vol. 102, pp. 3586-3616 (1998).*
Gogonea Quantum mechanical/quantum mechanical methods. I. A divide and conquer strategy for solving the Schrodinger equation for large molecular systems using a composite density functional-semiempirical Hamiltonian Journal of Chemical Physics vol. 113, pp. 5604-5613 (2000).*
Maynard et al. Reactivity of the HIV-1 nucleocapsid protein p7 zinc finger domains from the perspective of density-functional theory Proceedings of the National Academy of Sciences USA vol. 95, pp. 11578-11583 (1998).*
Nakajima et al. Flexible docking of a ligand peptide to a receptor protein by multicanonical molecular dynamics simulation Chemical Physics Letters vol. 278, pp. 297-301 (1997).*
Mortimer Chemistry A Conceptual Approach pp. 53-59 Van Nostrand Reinhold Co. New York (1971).*
Takeshi Onda et al., Type-specific Regulation of Adenylyl Cyclase, The Journal of Biological Chemistry, 276 No. 51 pp. 47785-47793, Dec. 21, 2001.
International Search Report PCT/JP2005/012200 dated Aug. 10, 2005 (Japanese Patent Office).
Transmittal letter from European Patent Office dated Jan. 14, 2009, forwarding Supplementary European Search Report in EP 05765321, and forwarding letter from Marks & Clerk to Shiga International Patent Office date-stamped received Feb. 2, 2009 (10 pages total).
Khandogin et al.,"Quantum Descriptors for Biological Macromolecules from Linear-Scaling Electronic Structure Methods", Proteins; Structure, Function, and Bioinformatics, vol. 56, No. 4, May 14, 2004, pp. 724-737.
Damjanovic et al., "Excitons in a Photosynthetic Light-Harvesting System: A Combined Molecular Dynamics, Quantum Chemistry, and Polaron Model Study", Physical Review. E, Statistical, Nonlinear, and Soft Matter Physics, The American Physical Society, Mar. 2002, vol. 65, No. 3, pt. 1, Mar. 2002, pp. 031919-1 through 031919-24.
Fuentealba et al., "Fukui Function in Chemistry" (online), Aug. 8, 2002, pp.1-43, Universidad de Chile Satniago, Chile, retrieved from the Internet: URL:http://www.nucleomileniocuantica.cl/personal/pfuentealba/parrvolu3.pdf>, retrieved Dec. 12, 2008.

* cited by examiner

*Primary Examiner* — John S Brusca
(74) *Attorney, Agent, or Firm* — Ostrolenk Faber LLP (57) ABSTRACT

A method for evaluating the binding of an evaluation target molecule with respect to a macromolecular compound based on numerical calculations and which detects the binding sites of the evaluation target molecule with respect to the macromolecular compound as a site where electronic states in a predetermined restricted region including the evaluation target molecule and the part of the macromolecular compound, which is adjacent to the evaluation target molecule, are unstable.

29 Claims, 4 Drawing Sheets

LUMO (Nucleophilic)

FIG. 4B

HOMO (Electrophilic)

FIG. 4C

BINDING EVALUATION METHOD FOR MACROMOLECULAR COMPOUND

CROSS REFERENCE TO RELATED APPLICATION

The present application is a 35 U.S.C. §371 national phase conversion of PCT/JP2005/012200 filed Jul. 1, 2005, which claims priority of Japanese application No. 2004-205746 filed Jul. 13, 2004, which are incorporated by reference. The PCT International application was published in the Japanese language.

TECHNICAL FIELD

The present invention relates to a binding evaluation method for a macromolecular compound.

BACKGROUND ART

In the development of a drug, the binding between a protein as one of the macromolecular compounds constituting a living body and a drug candidate agent, is evaluated. That is, a drug having a low affinity with respect to a protein is not appropriate as a drug candidate agent, and such drugs having a low affinity are excluded from the drug candidate agent. Moreover, as an evaluation method for the abovementioned affinity, X-ray structural analysis or a classical molecular dynamics method is generally used.

For example, in a prior art document below, there is disclosed study results of the binding mechanism between adenylate cyclase (type II) as a protein and forskolin as a drug candidate agent, as a case of affinity analysis using the classical molecular dynamics method. In this prior art document, by calculating each internal energy (potential energy+kinetic energy) of analytical models (systems) where various drug candidate agents such as forskolin are placed at the centre of the active site of adenylate cyclase using the classical molecular dynamics method, those having a relatively small internal energy (that is, those that stabilize the system energetically) are extracted as drug candidate agents having excellent affinity with respect to adenylate cyclase. At the same time, the document examines the binding site of forskolin, which is extracted as such and which is one of the drug candidate agents, with respect to adenylate cyclase.

[Non Patent Document 1]
Takeshi Onda et al., J. Bio. Chem., 276 (2001) 47785-47793

DISCLOSURE OF THE INVENTION

Problems to be Solved by the Invention

Although the abovementioned classical molecular dynamics method provides preliminary results of evaluation regarding the affinity between the active site of adenylate cyclase and drug candidate agents, the binding site of adenylate cyclase to drug candidate agents and binding state thereof cannot be elucidated solely by the results. For example, in the prior art document, although the binding site of forskolin with respect to the active site of adenylate cyclase is elucidated by substituting atoms or molecules, which are bound to the side chains of forskolin, with various atoms or molecules, this work is based on the experiments which require an extended period of time and vast amounts of labour and thus, is inefficient and not practical.

Moreover, although the approach of affinity evaluation in the prior art document is one evaluating the internal energy of an analytical model where drug candidate agents are placed in the centre of the active site of adenylate cyclase, there is a reliability problem and an evaluation approach with higher reliability is desired. That is, in the approach of affinity evaluation in the prior art document, since the effect which the position of drug candidate agents with respect to the active site of adenylate cyclase imposes on the internal energy is not considered, reliability thereof is low. The inventors of the present invention obtained calculation results showing that the internal energy is smaller in the analytical model where the position of forskolin is deviated from the centre of the active site of adenylate cyclase than that of the analytical model placing forskolin at the centre of the active site of adenylate cyclase.

The present invention addresses the abovementioned problems, with objects shown below.
(1) elucidate the binding site of a macromolecular compound with respect to evaluation target molecule more efficiently than in the past
(2) improve the reliability of the binding position of a macromolecular compound with respect to evaluation target molecule more than that in the past

Means for Solving the Problem

In order to achieve the above object, the present invention adopts a solution which is a method evaluating the binding of an evaluation target molecule with respect to a macromolecular compound based on numerical calculations and which detects the binding sites of the evaluation target molecule with respect to the macromolecular compound as a site where electronic states in a predetermined restricted region including the evaluation target molecule and the part of the macromolecular compound, which is adjacent to the evaluation target molecule, are unstable.

Effects of the Invention

According to the present invention, since the binding site of the evaluation target molecule with respect to the macromolecular compound is detected by numerical calculations as a site where electronic states in a predetermined restricted region including the evaluation target molecule and the part of the macromolecular compound, which is adjacent to the evaluation target molecule, are unstable, it is possible to numerically analyze the analysis target including the macromolecular compound having an extremely large number of electrons efficiently. Accordingly, it is possible to dramatically improve the analysis efficiency of binding sites compared to the conventional analytical approach of binding sites based on experiments.

BRIEF DESCRIPTION OF THE REFERENCE SYMBOLS

A: adenylate cyclase, B: forskolin, G: restricted region

BEST MODE FOR CARRYING OUT THE INVENTION

Hereunder is a description of one embodiment of the present invention, with reference to the drawings.

The present embodiment relates to an evaluation method for the binding between the active site of a protein as a macromolecular compound, more specifically adenylate cyclase (A), and a drug candidate agent as an evaluation target molecule, more specifically forskolin (B).

Figure 1:
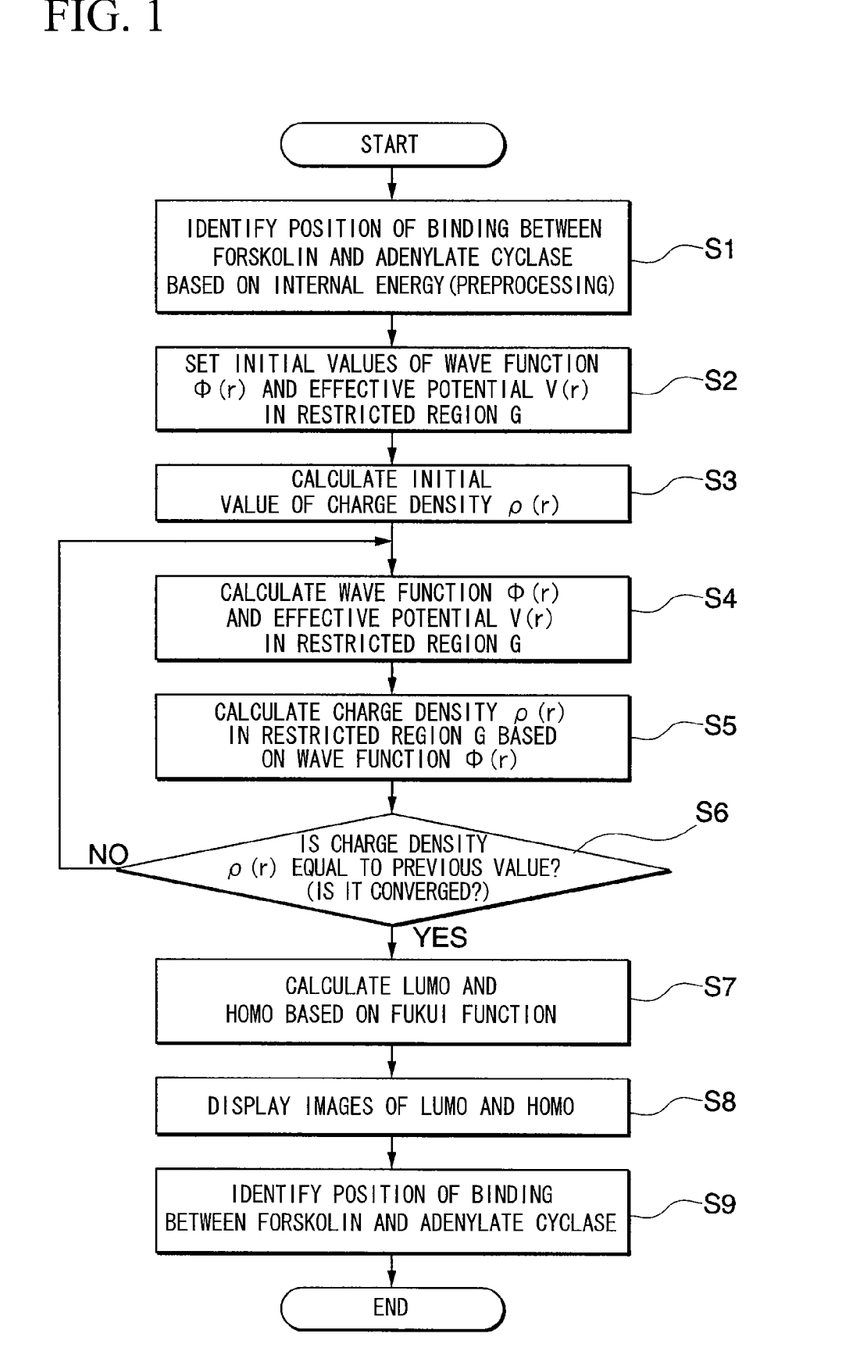
FIG. 1 is a flow chart showing a processing procedure of a binding evaluation method according to one embodiment of the present invention.

FIG. 1 is a flow chart showing a processing procedure of the present binding evaluation method. In this processing procedure, step S1 shows a process for detecting binding positions as preprocessing and steps S2 to S9 show processes for detecting binding sites as actual processing.

In the process for detecting binding positions, binding positions are identified by evaluating the internal energy (potential energy+kinetic energy) of analytical models formed from adenylate cyclase (A) and forskolin (B) based on the numerical analysis using a computer (step S1).

Figure 2:
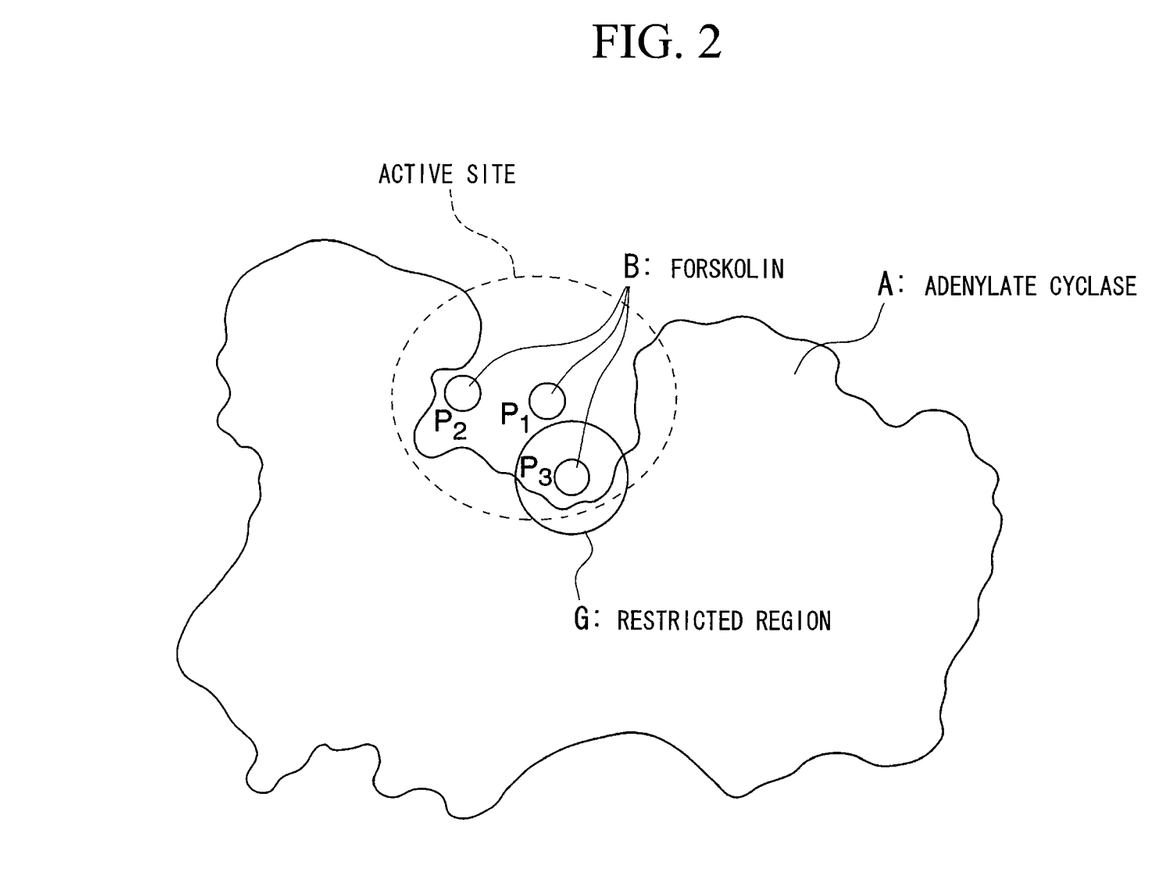
FIG. 2 is a schematic diagram of an analytical model for identifying the binding position of forskolin (B) with respect to the active site of adenylate cyclase (A) in one embodiment of the present invention.

FIG. 2 is a schematic diagram schematically showing an analytical model for identifying binding positions. When forskolin (B) and adenylate cyclase (A) are bound, forskolin (B) binds to any place in the active site of adenylate cyclase (A) shown with broken lines. In the present binding evaluation method, each internal energy of target models for analysis in a state where a plurality of positions of forskolin (B) with respect to the active site are set is numerically calculated using the classical molecular dynamics method and the position of forskolin (B) corresponding to the internal energy, which has the minimum value among the internal energies corresponding to each position, is identified as the binding position of forskolin (B) in the active site of adenylate cyclase (A).

For example, although positions of forskolin (B) $P_1$, $P_2$, and $P_3$ shown in FIG. 2 are 3 places selected as representatives, internal energies of each target model for analysis where forskolin (B) is placed at each of positions $P_1$, $P_2$, and $P_3$ will be those below.

Position $P_1$: —122477.433 kcal/mol
Position $P_2$: —120889.463 kcal/mol
Position $P_3$: —124151.413 kcal/mol As is apparent from the intercomparison of these internal energies, the internal energy is at its lowest when forskolin (B) is located at position $P_3$ among the 3 positions $P_1$, $P_2$, and $P_3$. Although internal energies are determined for a plurality of positions other than these 3 positions $P_1$, $P_2$, and $P_3$, as a result, internal energy showed the minimum value when forskolin (B) is located at position $P_3$. That is, since forskolin (B) binds to the active site of adenylate cyclase (A) in the most internally energetic stabilized state when placed at position $P_3$ among the active sites, it is identified that the binding position of forskolin (B) with respect to the active site is position $P_3$.

When the binding position of forskolin (B) is identified as described so far, the binding site of forskolin (B) with respect to adenylate cyclase (A) in the binding position is identified based on the processing of steps S2 to S9. Among these steps, steps S2 to S6 are processes determining the charge density ρ(r) of a predetermined restricted region (G) including forskolin (B) and the parts of adenylate cyclase (A), which is adjacent to forskolin (B), by determining the wave function Φ (r) regarding the restricted region (G) via numerical calculations using a computer (charge density calculating process). Note that in the wave function Φ (r) and charge density ρ(r), r is a variable showing the coordinates in a 3-dimensional space.

Figure 3:
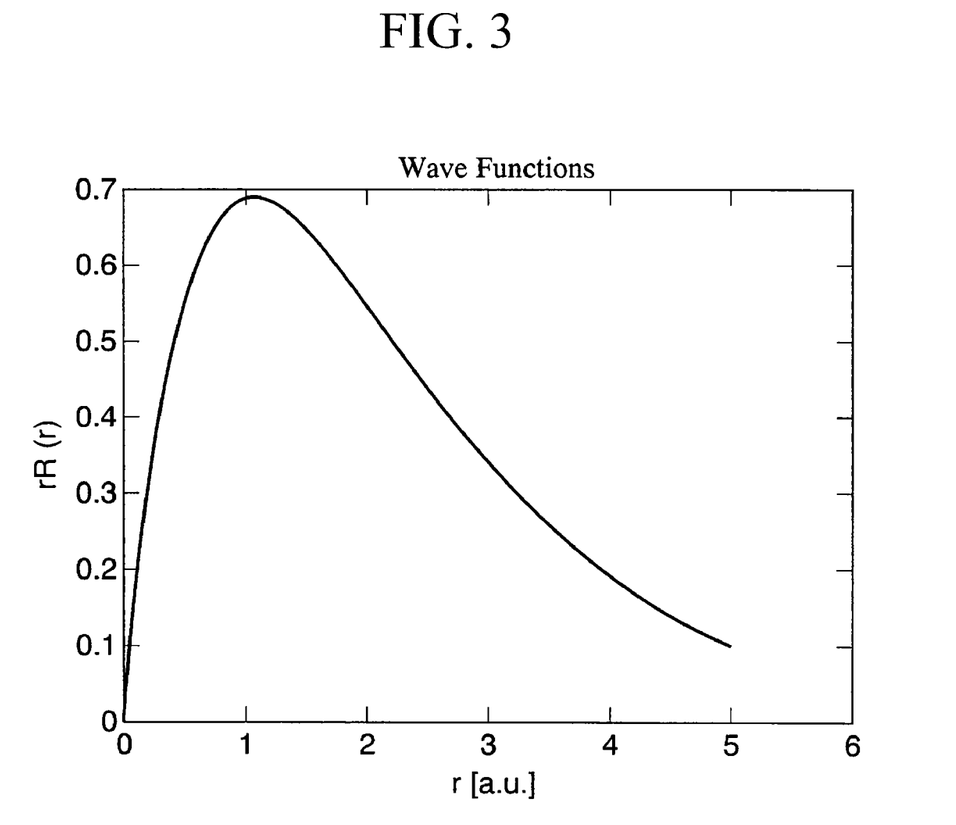
FIG. 3 is a graph showing variations in wave function of electrons in the 1s orbital which belongs to a hydrogen atom as one example of the variation characteristics of wave function in the radial direction in one embodiment of the present invention.

The setting method of the abovementioned restricted region (G) will be described by referring also to FIG. 3. FIG. 3 is a graph where the wave function R(k) of the electron, which belongs to a hydrogen atom (the electron in the 1 s orbital), is numerically calculated by taking the distance r in the radial direction as a variable when setting the atomic nucleus as a base point. Note that in this graph, the vertical axis shows values where the radial wave function R(r) is multiplied by the distance r for convenience and the horizontal axis shows the distance from the atomic nucleus using the unit a.u. (1 a.u.=0.529 Å).

The radial wave function R(r) shows, as is well-known, the existence probability of electrons and also in this graph, although the probability is "0" at the position of the atomic nucleus, it increases as the distance r increases and after reaching the maximum value at a certain distance, which is relatively close to the atomic nucleus, it gradually decreases and approach "0" asymptotically. In other words, the distance range where the radial wave function R(r) may take on significant values is limited to the vicinity of the atomic nucleus and in distant ranges outside this range, the function can be regarded as almost "0". Such variation characteristics of the radial wave function R(r) is found not only in the electron belonging to the hydrogen atom but also in electrons belonging to other atoms or other orbitals.

In the present embodiment, by taking such variation characteristics of the wave function into consideration, the distance range where the wave function may take on significant values is set as the abovementioned restricted region (G). In other words, the range of variable r, which represents 3-dimensional positions, is restricted to the region where the radial wave function R(r) may take on sufficiently large values and the charge density ρ(r) of the restricted region (G) is calculated by determining only the wave function in this restricted region (G). Although the distance range where the radial wave function R(r) may take on significant values differs to some extent depending on the type of atoms and electron orbitals, at the distance distant from the atomic nucleus by 10 to 20 Å, the radial wave functions R(r) of almost all the atoms and electrons in electron orbitals can be considered to approach "0" asymptotically.

From the viewpoints above, in the present embodiment, a threshold value of 10 to 20 Å is adopted to define the restricted region (G) and by this procedure and by taking the atomic nuclei of each atom constituting forskolin (B) as the centre, the 3-dimensional space within the radius of 10 to 20 Å is set as the restricted region (G). This restricted region (G) is a 3-dimensional space including forskolin (B) and the parts of adenylate cyclase (A) adjacent to forskolin (B). By setting such a restricted region (G), computational complexity in the charge-density calculating process described below is reduced to a large extent compared to the case where the restriction region (G) is not provided.

In the charge-density calculating process, each of the initial values of the wave function $\Phi(r)$ and effective potential $V(r)$ regarding the restricted region (G) are set at the beginning (step S2) and the initial values of charge density $\rho(r)$ based on all the electrons in the restricted region (G) are calculated by assigning the initial values of wave function $\Phi(r)$ to the formula (1) below (step S3).

$$\rho(r)=\Sigma\Phi^*(r)\Phi(r) \quad (1)$$

By solving the Schrödinger wave equation (2) below based on the abovementioned initial values of the effective potential $V(r)$ and those of charge density $\rho(r)$, the wave function $\Phi(r)$ in the restricted region (G) is calculated (step S4). Note that in this Schrödinger wave equation (2), $\epsilon$ is expected values of internal energy.

$$\left[-\frac{1}{2}\nabla^2 + V\{r, \rho(r)\}\right]\Phi(r) = \varepsilon\Phi(r) \quad (2)$$

Charge density $\rho(r)$ is determined by assigning the wave function $\Phi(r)$ derived from the Schrödinger wave equation (2) to the formula (1) (step S5) and whether or not this charge density $\rho(r)$ equals the charge density $\rho(r)$ derived in the previous calculation is determined (step S6). If the two are not equal (when the result is "NO"), the procedures of steps S4 and S5 are repeated by taking the wave function $\Phi(r)$ and effective potential $V(r)$ derived by solving the Schrödinger wave equation (2) in step S5 as new initial values to determine the new wave function $\Phi(r)$ and charge density $\rho(r)$.

In other words, by repeatedly solving the Schrödinger wave equation (2) until the charge density $\rho(r)$ currently determined equals the charge density $\rho(r)$ previously determined, the charge density $\rho(r)$ which satisfies the Schrödinger wave equation (2), that is, which equals the previous charge density $\rho(r)$ is determined.

When such a charge density $\rho(r)$ is derived, the determination in step S6 will become "YES" and by assigning this charge density $\rho(r)$ to Fukui functions (3) and (4) below, LUMOf$^+$(r) and HOMOf$^-$(r) as values of Fukui functions (3) and (4) in the restricted region (G) are calculated (step S7). LUMO: lowest unoccupied molecular orbital (Nucleophilic) (3)

$$f^+(r) = \frac{1}{\Delta N}\{\rho_{N+\Delta}(r) - \rho(r)\}$$

HOMO: highest occupied molecular orbital (Electrophilic) (4)

$$f^-(r) = \frac{1}{\Delta N}\{\rho_N(r) - \rho_{N-\Delta}(r)\}$$

These LUMOf$^+$(r) and HOMOf$^-$(r) show the degree of instability of electronic states in the restricted region (G) and while LUMOf$^+$(r) shows the degree of electron-accepting property (property to receive electrons), HOMOf$^-$(r) shows the degree of electron-donating property (property to release electrons). Such LUMOf$^+$(r) and HOMOf$^-$(r) are displayed by images (step S8) and based on this displayed result, the binding site between forskolin (B) and adenylate cyclase (A) in the restricted region (G), that is, which atom constituting forskolin (B) binds to which atom constituting adenylate cyclase (A) is identified (step S9).

Figure 4A:
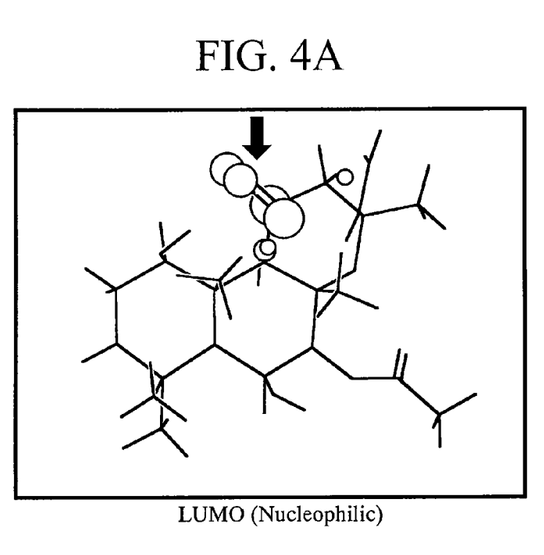
FIG. 4A is a characteristic chart where LUMOf⁺(r) and HOMOf⁻(r) in the forskolin vicinity-region are shown as isosurfaces in one embodiment of the present invention.
Figure 4B:
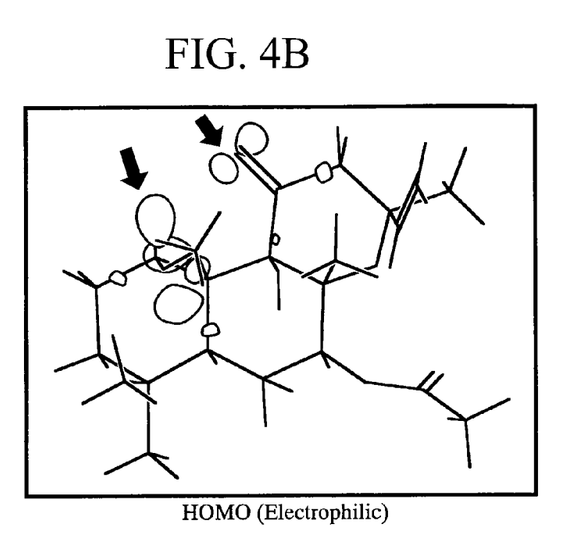
FIG. 4B is a characteristic chart where LUMOf⁺(r) and HOMOf⁻(r) in the forskolin vicinity-region are shown as isosurfaces in one embodiment of the present invention.
Figure 4C:
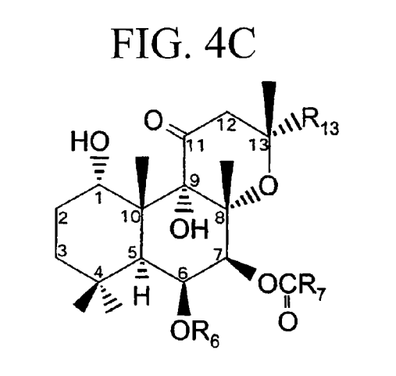
FIG. 4C is a molecular structure of forskolin derivatives.

FIGS. 4A to 4C are characteristic charts where LUMOf$^+$(r) and HOMOf$^-$(r) in the forskolin vicinity-region inside the restricted region (G) are shown as "Isosurfaces". That is, in these characteristic charts, the part (spatial region) which corresponds to LUMOf$^+$(r) and HOMOf$^-$(r) that are equivalent to 90% of the maximum value in this forskolin vicinity-region is set as "Isosurface" and this "Isosurface" is displayed by being made to correspond to the molecular structure of forskolin (B).

Although FIG. 4A shows the abovementioned "Isosurface" regarding LUMOf$^+$(r), as is apparent when this FIG. 4A is contrasted with FIG. 4C, which shows the molecular structure of forskolin (B), the arrow part displaying the "Isosurface" as a relatively large space in FIG. 4A is the part corresponding to an oxygen atom (O), which is one of the side chains of forskolin (B).

On the other hand, although FIG. 4B shows the "Isosurface" regarding HOMOf$^-$(r), as is apparent when this FIG. 4B is contrasted with FIG. 4C, which shows the molecular structure of forskolin (B), the arrow part displaying the "Isosurface" as a relatively large space in FIG. 4B is the part corresponding to an OH group (OH), which is one of the side chains of forskolin (B).

From this FIG. 4, it is clear that the oxygen atom (O), which is a side chain of forskolin (B), has a considerably high electron-accepting property among the respective atoms constituting forskolin (B) and the OH group (OH), which is a side chain of forskolin (B), has a considerably high electron-donating property among the respective atoms constituting forskolin (B). Since the binding between forskolin (B) and the active site of adenylate cyclase (A) is formed via covalent bonds of atoms, each of which belongs to the two substances, the abovementioned oxygen atom (O) and OH group (OH) of forskolin (B) are considered to be the sites which bind to the active site of adenylate cyclase (A) (binding sites).

The result of the present binding evaluation method showing that these oxygen atom (O) and OH group (OH) in forskolin (B) are the binding sites with the active site of adenylate cyclase (A) completely coincide with the result (experimental result) in the prior art document, which is shown as a conventional art.

On the other hand, by calculating LUMOf$^+$(r) and HOMOf$^-$(r) regarding the part of adenylate cyclase, which is adjacent to forskolin (B), in the restricted region (G) based on the abovementioned Fukui functions (2) and (3) and also by displaying as "Isosurface", the sites (atoms) which have high electron-accepting property and electron-donating property in the part of adenylate cyclase, which is adjacent to forskolin (B), are identified. This result also completely coincides with the result (experimental result) in the prior art document, which is shown as a conventional art. Note that the characteristic chart showing LUMOf$^+$(r) and HOMOf$^-$(r) regarding the part of adenylate cyclase (A), which is adjacent to forskolin (B), in the restricted region (G) as "Isosurface" is omitted because atoms are intricately present and are difficult to illustrate.

In other words, the present binding evaluation method, which identifies the binding sites between the active site of adenylate cyclase (A) and forskolin (B) based on LUMOf$^+$(r) and HOMOf$^-$(r) regarding forskolin (B) and the part of adenylate cyclase (A) that is adjacent to forskolin (B) in the restricted region (G), is an evaluation approach of binding sites which derives results that completely coincide with experimental results and which is sufficiently effective.

Moreover, since the present binding evaluation method makes only atoms present in the restricted region (G) as targets for numerical analysis, it is possible to reduce the time required for calculating wave function Φ(r) and charge density ρ(r) to a large extent compared to the case where all the atoms constituting forskolin (B) and adenylate cyclase (A) are made targets for numerical analysis. Accordingly, it is possible to dramatically improve the analysis efficiency of binding sites compared to the conventional analytical approach of binding sites based on experiments.

It should be noted that the present invention is not limited to the above embodiment and for example, modifications such as the following may be considered.

(1) Although the above embodiment is one regarding the binding between forskolin (B) as an evaluation target molecule and adenylate cyclase (A) as one of macromolecular compounds, the present invention is not limited to this. That is, macromolecular compounds are not limited to adenylate cyclase (A) but may be other proteins or other macromolecular compounds and also the evaluation target molecules are not limited to forskolin (B).

(2) In the above embodiment, the restricted region (G) is set as the 3-dimensional spaces which have atomic nuclei of each atom constituting forskolin (B) as the centre and ranges within the radius of 10 to 20 Å by adopting 10 to 20 Å as a threshold value to define the restricted region (G), and by setting such a restricted region (G), analysis efficiency is dramatically improved by reducing computational complexity in the calculation of charge density ρ(r) required for the calculation of LUMOf$^+$(r) and HOMOf$^-$(r) considerably. Setting of such a restricted region (G) is based on the knowledge that it is possible to consider the wave function Φ(r) of electrons which belong to the atoms constituting forskolin, to approach "0" asymptotically in the distance which is 10 to 20 Å distant from atomic nuclei.

However, the above threshold value defining the restricted region (G), that is, the distance where the wave function Φ(r) is regarded to take on significant values, is not limited to 10 to 20 Å. Moreover, since the variation characteristics of wave function Φ(r) differ depending on the type of constituting atoms or electron orbitals of forskolin, the distance where wave function Φ(r) takes on significant values differs in response to the type of constituting atoms or electron orbitals. Accordingly, threshold values defining the restricted region (G) may be set for each type of constituting atoms or electron orbitals.

(3) Although the site where the electronic state is unstable is identified using Fukui functions (3) and (4) in the above embodiment, the method for identifying the site where the electronic state is unstable is not limited to Fukui functions (3) and (4). The site where the electronic state is unstable may be identified using other evaluation functions.

INDUSTRIAL APPLICABILITY

According to the present invention, since the binding site of an evaluation target molecule with respect to a macromolecular compound is detected by numerical calculations as a site where electronic states in a predetermined restricted region including the evaluation target molecule and the part of the macromolecular compound, which is adjacent to the evaluation target molecule, are unstable, it is possible to numerically analyze the analysis target including macromolecular compounds having an extremely large number of electrons efficiently. Accordingly, it is possible to dramatically improve the analysis efficiency of binding sites compared to the conventional analytical approach of binding sites based on experiments.

The invention claimed is:

1. A binding evaluation method comprising:
a step S1 of detecting a binding position of an evaluation target molecule in which internal energy, calculated using a classical molecular dynamics method, of a targeted model for analysis formed from a macromolecular compound and the evaluation target molecule takes on a minimum value as a binding position with respect to an active site, as a preprocess;
a step S2 of setting each of initial values of a wave function Φ(r) and an effective potential V(r) regarding a restricted region (G);
a step S3 of calculating the initial values of charge density ρ(r) based on all electrons in the restricted region (G) by assigning the initial values of wave function Φ(r) to a formula (1):

$$\rho(r) = \Sigma \Phi^*(r)\Phi(r) \quad (1);$$

a step S4 of calculating the wave function Φ(r) in the restricted region (G) by solving a Schrödinger wave equation (2):

$$\left[-\frac{1}{2}\nabla^2 + V\{r, \rho(r)\}\right]\Phi(r) = \varepsilon\Phi(r); \quad (2)$$

based on the initial values of the effective potential V(r) and those of charge density ρ(r);
a step S5 of determining the charge density ρ(r) by assigning the wave function Φ(r) derived from the Schrödinger wave equation (2) to the formula (1);
a step of S6 of determining whether or not the charge density ρ(r) equals the charge density ρ(r) derived in the previous calculation and determining the charge density ρ(r) which satisfies the Schrödinger wave equation (2) and equals the previous charge density ρ(r) by repeatedly solving the Schrödinger wave equation (2) until the charge density ρ(r) currently determined equals the charge density ρ(r) previously determined;
a step S7 of calculating LUMOf$^+$(r) and HOMOf$^-$(r) as values of Fukui functions (3) and (4):

$$f^+(r) = \frac{1}{\Delta N}\{\rho_{N+\Delta}(r) - \rho(r)\} \quad (3)$$

$$f^-(r) = \frac{1}{\Delta N}\{\rho_N(r) - \rho_{N-\Delta}(r)\}; \quad (4)$$

in the restricted region (G) by assigning the charge density ρ(r) to Fukui functions (3) and (4);
a step S8 of displaying the LUMOf$^+$(r) and the HOMOf$^-$(r) by images; and
a step S9 of identifying a binding site between the evaluation target molecule and the macromolecular compound, wherein the steps S1 to S9 are based on at least numerical calculations using a computer.

2. The binding evaluation method according to claim 1, wherein the restricted region is a region where a wave function of electrons in the evaluation target molecule takes on significant values, and the region where a wave function of electrons in the evaluation target molecule takes on significant values is a 3-dimensional space within a radius of 10 to 20 Å by taking an atomic nucleus of each atom constituting the evaluation target molecule as the center.

3. The binding evaluation method according to claim 1, wherein the macromolecular compound is a protein.

4. The binding evaluation method according to claim 2, wherein the macromolecular compound is a protein.

5. The binding evaluation method according to claim 1, wherein the evaluation target molecule is a drug candidate agent.

6. The binding evaluation method according to claim 2, wherein the evaluation target molecule is a drug candidate agent.

7. The binding evaluation method according to claim 3, wherein the evaluation target molecule is a drug candidate agent.

8. The binding evaluation method according to claim 4, wherein the evaluation target molecule is a drug candidate agent.

9. The binding evaluation method according to claim 1, wherein the macromolecular compound is adenylate cyclase, and an evaluation target molecule is forskolin.

10. The binding evaluation method according to claim 1, wherein the binding position is identified by evaluating the internal energy comprising potential energy plus kinetic energy of analytical models formed from the macromolecular compound and the evaluation target molecule using a computer.

11. The binding evaluation method according to claim 1, wherein in the wave function $\Phi(r)$ and charge density $\rho(r)$, r is a variable showing the coordinates in a 3-dimensional space.

12. The binding evaluation method according to claim 1, wherein the electronic state in the restricted region is evaluated with respect to an electron in a 1s orbital of a hydrogen atom and also electrons belonging to other atoms.

13. The binding evaluation method according to claim 1, wherein the restricted region is set as the distance range where the wave function may take on significant values.

14. The binding evaluation method according to claim 1, wherein the restricted region is set as the distance range where the range of variable r, which represents 3-dimensional positions, comprises the region where a radial wave function R(r) may take on values in excess of a predetermined threshold, and the charge density $\rho(r)$ of the restricted region is calculated by determining only the wave function in this restricted region.

15. The binding evaluation method according to claim 1, wherein the restricted region is set such that a computational complexity in a charge-density calculating process of the steps S2 to S6 is substantially reduced compared to a case where the restriction region is not provided.

16. The binding evaluation method according to claim 1, wherein a binding site interaction between the macromolecular compound and the target evaluation molecule comprises a covalent bond.

17. The binding evaluation method according to claim 1, wherein a size of a restricted region is selected based on characteristics of a wave function $\Phi(r)$ of atoms in at least the target evaluation molecule.

18. The binding evaluation method according to claim 1, wherein a size of a restricted region is selected based on characteristics of a wave function $\Phi(r)$ of atoms in at least the macromolecular compound.

19. The binding evaluation method according to claim 14, wherein the radial wave function R(r) is numerically calculated by taking the distance r in a radial direction as a variable when setting an atomic nucleus as a base point.

20. The binding evaluation method according to claim 19, wherein the distance r in the radial direction is 10 to 20 Å.

21. A binding evaluation method comprising:
  detecting a binding position of an evaluation target molecule with respect to an active site of an a macromolecular compound, in which internal energy takes on a minimum value, using a classical molecular dynamics method, calculated using a targeted model formed based on the macromolecular compound and the evaluation target molecule;
  setting initial values of a wave function $\Phi(r)$ and an effective potential V(r) regarding a restricted region (G) with respect to the detected binding position;
  calculating the initial values of a charge density $\rho(r)$ based on all electrons in the restricted region (G), by assigning the initial values of wave function $\Phi(r)$;
  calculating the wave function $\Phi(r)$ in the restricted region (G) by solving a Schrödinger wave equation;
  based on the initial values of the effective potential V(r) and the charge density $\rho(r)$;
  iteratively updating the charge density $\rho(r)$ by assigning the wave function $\Phi(r)$ derived from the Schrödinger wave equation, until convergence;
  calculating a values of a plurality of Fukui functions in the restricted region (G) by assigning the charge density $\rho(r)$ to the plurality of Fukui functions; and
  identifying a binding site of the evaluation target molecule at the macromolecular compound, wherein at least the iteratively updating are based on at least numerical calculations using a computer.

22. The method according to claim 21, wherein the charge density is expressed according to a formula (1):

$$\rho(r) = \Sigma \Phi^*(r) \Phi(r) \quad (1),$$

the Schrödinger wave equation is expressed according to a formula (2):

$$\left[-\frac{1}{2}\nabla^2 + V\{r, \rho(r)\}\right]\Phi(r) = \varepsilon\Phi(r). \quad (2)$$

and the plurality of Fukui functions comprise (3) and (4):

$$f^+(r) = \frac{1}{\Delta N}\{\rho_{N+\Delta}(r) - \rho(r)\} \quad (3)$$

$$f^-(r) = \frac{1}{\Delta N}\{\rho_N(r) - \rho_{N-\Delta}(r)\}, \quad (4)$$

which are used to calculate at least LUMOf$^+$(r) and HOMOf$^-$(r).

23. The method according to claim 22, further comprising displaying the LUMOf$^+$(r) and the HOMOf$^-$(r).

24. The method according to claim 22, wherein the restricted region is a 3-dimensional space where the wave function $\Phi(r)$ takes on significant values, having a radius of 10 to 20 Å about an atomic nucleus of each atom constituting the evaluation target molecule.

25. The method according to claim 22, wherein the binding position is identified by evaluating the internal energy comprising potential energy plus kinetic energy of analytical models formed from the macromolecular compound and the evaluation target molecule using a computer.

26. The method according to claim 21, wherein the electronic state in the restricted region is evaluated with respect to an electron in a 1s orbital of a hydrogen atom and also electrons belonging to other atoms.

27. The method according to claim 21, wherein a binding site interaction between the macromolecular compound and the target evaluation molecule comprises a covalent bond.

28. The method according to claim 21, wherein a range of a restricted region is selected based on characteristics of a wave function $\Phi(r)$ of atoms in at least the target evaluation molecule and the macromolecular compound.

29. The method according to claim 21, wherein the radial wave function $R(r)$ is numerically calculated for r within a predefined radial distance from an atomic nucleus.

* * * * *